US008703458B2

(12) United States Patent
Heller et al.

(10) Patent No.: US 8,703,458 B2
(45) Date of Patent: *Apr. 22, 2014

(54) METHOD COMPRISING CO-CROSSLINKING POLYANILINE, POLYMER ACID AND REDOX ENZYME TO PRODUCE POLYMERIC MATRIX

(71) Applicant: Abbott Diabetes Care Inc., Alameda, CA (US)

(72) Inventors: Adam Heller, Austin, TX (US); Benjamin J. Feldman, Oakland, CA (US); Nicolas Mano, Austin, TX (US); Yueh-Lin Loo, Lawrenceville, NJ (US)

(73) Assignee: Abbott Diabetes Care Inc., Aladema, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/756,009

(22) Filed: Jan. 31, 2013

(65) Prior Publication Data

US 2013/0203147 A1 Aug. 8, 2013

Related U.S. Application Data

(63) Continuation of application No. 13/326,071, filed on Dec. 14, 2011, now Pat. No. 8,383,361, which is a continuation of application No. 12/114,359, filed on May 2, 2008, now Pat. No. 8,080,385.

(60) Provisional application No. 60/916,440, filed on May 7, 2007, provisional application No. 60/924,196, filed on May 3, 2007, provisional application No. 60/924,197, filed on May 3, 2007.

(51) Int. Cl.
*C12N 11/04* (2006.01)
*C12N 11/08* (2006.01)
*C12Q 1/54* (2006.01)
*C12Q 1/26* (2006.01)
*C12Q 1/32* (2006.01)
*C12Q 1/28* (2006.01)

(52) U.S. Cl.
USPC ............... 435/182; 435/180; 435/14; 435/25; 435/26; 435/28

(58) Field of Classification Search
None
See application file for complete search history.

(56) References Cited

U.S. PATENT DOCUMENTS

| | | | |
|---|---|---|---|
| 5,356,786 | A | 10/1994 | Heller et al. |
| 5,665,222 | A | 9/1997 | Heller et al. |
| 5,840,214 | A | 11/1998 | Kinlen |
| 5,972,199 | A | 10/1999 | Heller et al. |
| 6,121,009 | A | 9/2000 | Heller et al. |
| 6,383,415 | B1 | 5/2002 | Angelopoulos et al. |
| 6,514,718 | B2 | 2/2003 | Heller et al. |
| 6,576,461 | B2 | 6/2003 | Heller et al. |
| 6,638,716 | B2 | 10/2003 | Heller et al. |
| 6,656,388 | B1 | 12/2003 | Yang et al. |
| 6,689,265 | B2 | 2/2004 | Heller et al. |
| 6,730,212 | B1 | 5/2004 | Yamagishi et al. |
| 6,881,551 | B2 | 4/2005 | Heller et al. |
| 7,018,735 | B2 | 3/2006 | Heller |
| 7,058,437 | B2 | 6/2006 | Buse et al. |
| 7,545,272 | B2 | 6/2009 | Goodnow et al. |

OTHER PUBLICATIONS

Borole et al., "Glucose oxidase electrodes of polyaniline, poly(o-toluidine) and their copolymer as a biosensor: a comparative study," Polymers for Advanced Technologies, vol. 15, pp. 306-312 (2004).
Brahim et al., "Chemical and Biological Sensors Based on Electrochemical Detection Using Conducting Electroactive Polymers," Microchimica Acta, vol. 143, pp. 123-137 (2003).
Chaubey et al., "Co-immobilization of lactate oxidase and lactate dehydrogenase on conducting polyaniline films," Analytica Chimica Acta, vol. 407, pp. 97-103 (2000).
Cooper & Hall, "Catalytic Reduction of Benzoquinone at Polyaniline and Polyaniline/Enzyme Films," Electroanalysis, vol. 5, pp. 385-397 (1993).
Epstein & MacDiarmid, "Polaron and Bipolaron Defects in Polymers: Plyaniline," Journal of Molecular Electronics, vol. 4, pp. 161-165 (1988).
Garjonyte & Malinaiskas, "Amperometric glucose biosensors based on Prussian Blue- and polyaniline-glucose oxidase modified electrodes," Biosensors and Bioelectronics, vol. 15, pp. 445-451 (2000).
Granot et al., "Enhanced Bioelectrocatalysis Using Single-Walled Carbon Nanotubes (SWCNTs)/Polyaniline Hybrid Systems in Thin-Film and Microrod Structures Associated with Electrodes," Electroanalysis, vol. 18, No. 1, pp. 26-34 (2006).
Hall et al., "Investigating Polymers and Conducting Metals as Transduction Mediators or Immobilization Matrices," Electroanalysis, vol. 7, pp. 830-837 (1995).
Han et al., "Combination of Electrochemistry with Concurrent Reduction and Substitution Chemistry to Provide a Facile and Versatile Tool for Preparing Highly Functionalized Polyanilines," American Chemical Society, vol. 11, pp. 480-486 (1999).

(Continued)

*Primary Examiner* — David M Naff
(74) *Attorney, Agent, or Firm* — Edward J. Baba; Khin K. Chin; Bozicevic, Field & Francis LLP

(57) ABSTRACT

A polymer matrix that may coated on an electrode is created by co-crosslinking (1) an adduct of a polyaniline formed by templated oxidative polymerization on a polymer acid; (2) a water-soluble crosslinker; and (3) a redox enzyme. The polymer matrix may be hydrated, and the absorbed water may make it permeable to, for example, glucose. The polyaniline may be polyaniline itself or a substituted polyaniline; the water-soluble crosslinker may be poly(ethylene glycol) diglycidyl ether, and the redox enzyme may be glucose oxidase. The polymer matrix may be produced by co-crosslinking (1) an adduct of an electrically conductive polymer and a polymer acid; (2) a water-soluble crosslinker; and (3) a redox enzyme in a single step at an about neutral pH, curing by drying. After hydration, the crosslinked polymer matrix may form a 3-dimensional glucose-permeable bioelectrocatalyst, catalyzing the electrooxidation of glucose.

17 Claims, 6 Drawing Sheets

(56) References Cited

OTHER PUBLICATIONS

Heller, "Electron-conducting redox hydrogels: design, characteristics and synthesis," ScienceDirect, vol. 10, pp. 664-672 (2006).

Horanyi & Inzelt, "Anion-Involvement in Electrochemical Transformations of Polyaniline. A Radiotracer Study," Electrochemica Acta, vol. 33, pp. 947-952 (1988).

Hua & Ruckenstein, "Water-Soluble Conducting Poly(ethylene oxide)-Grafted Polydiphenylamine Synthesis through a "Graft Onto" Process," Macromolecules, vol. 36, pp. 9971-9978 (2003).

Inzelt, "Temperature dependence of the voltammetric response of polyaniline film electrodes," Journal of Electroanal. Chem., vol. 279, pp. 169-178 (1990).

Katakis et al., "Electrostatic Control of the Electron Transfer Enabling Binding of Recombinant Glucose Oxidase and Redox Polyelectrolytes," Journal of the American Chemical Society, vol. 116, pp. 3617-3618 (1994).

Lee et al., "High-Resolution Characterization of Pentacene/Polyaniline Interfaces in Thin-Film Transistors," Advanced Functional Materials, vol. 16, pp. 2409-2414 (2006).

Lee et al., "Metallic transport in polyaniline," Nature, vol. 441, pp. 65-68 (May 4, 2006).

Mano et al., "On the parameters affecting the characteristics of the 'wired' glucose oxidase anode," Journal of Electroanalytical Chemistry, vol. 574, pp. 347-357 (2005).

Mao et al., "Long Tethers Binding Redox Centers to Polymer Backbones Enhance Electron Transport in Enzyme 'Wiring' Hydrogels," Journal of the American Chemical Society, vol. 125, pp. 4951-4957 (2003).

Pan et al., "Polyaniline glucose oxidase biosensor prepared with template process," Science Direct, vol. 102, pp. 325-330 (2004).

Parente et al., "Glucose Biosensor Using Glucose Oxidase Immobilized in Polyaniline," Applied Biochemistry and Biotechnology, vol. 37, pp. 267-273 (1992).

Simon et al., "Oxidation of NADH produced by a lactate dehydrogenase immobilised on poly(aniline)-poly(anion) composite films," Journal of Electroanalytical Chemistry, Vol. 538-539, pp. 253-259 (2002).

Yoo et al., "Improving the electrical conductivity of polymer acid-doped polyaniline by controlling the template molecular weight," Journal of Materials Chemistry, vol. 17, pp. 1268-1275 (2007).

METHOD COMPRISING CO-CROSSLINKING POLYANILINE, POLYMER ACID AND REDOX ENZYME TO PRODUCE POLYMERIC MATRIX

This application is a continuation of application Ser. No. 13/326,071, filed Dec. 14, 2011, now U.S. Pat. No. 8,383,361 which is a continuation of application Ser. No. 12/114,359, filed May 2, 2008, now U.S. Pat. No. 8,080,385, which claims priority from Provisional Application No. 60/916,440 filed May 7, 2007 and Provisional Application Nos. 60/924,196 and 60/924,197 filed May 3, 2007 the entire disclosure(s) of the prior applications is incorporated herein by reference.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. N00014-02-1-0144 awarded by the Office of Naval Research.

BACKGROUND OF THE INVENTION (1) Field of the Invention

The present invention is directed to sensors, and, more specifically to a redox hydrogel useful in sensors.

(2) Description of Related Art

In vivo monitoring of glucose is relevant to the management of diabetes. Subcutaneous biosensors can be used to intermittently or continuously monitor the glucose concentration of people in need of such monitoring, particularly people suffering of diabetes. The sensors are also useful in alerting their users and/or medical professionals to hypoglycemia and/or hyperglycemia, and/or impending hypoglycemia and/or hyperglycemia. They are useful in acquiring information about glucose concentration excursions following and/or during events like meals, exercise and sleep, from which an individual's need to take corrective action, such as injecting a particular insulin dose and/or consuming a particular amount of source of glucose at a particular time can be deduced, and are useful in counseling the user to inject the particular insulin dose and/or consume the particular amount of glucose source. Eventually the sensors could become a core component of feedback loops for automatic or manually controlled maintenance of glucose concentrations within a defined range. For example, when used in conjunction with an insulin pump, a specified amount of insulin may be delivered from the pump if the sensor glucose reading is above a set value.

Continuously or intermittently operating glucose sensors, including sensors implanted in the human body, are sought for the management of Type I diabetes. For example, such sensors may provide a warning of imminent or actual hypoglycemia, and hence provide for its avoidance. Hypoglycemia can be fatal, and frequent or continuous monitoring of glucose in diabetic patients is needed in order to ensure that they remain at or near normal blood glucose levels.

Depending on its hydration, polyaniline (PANI) conducts charge carriers by two different mechanisms. When not hydrated, it conducts through one-dimensional bands. Such conduction requires at least one-dimensionally semicrystalline PANI. See Epstein, A., et al. J. MOLECULAR ELECTRONICS 1988, 4, 161-65; Lee, K. et al. NATURE 2006, 441, 65-68. Hydration disrupts the parallel alignment of the chains, and lowers the conduction. When dissolved, PANI behaves as a polymeric redox couple, and if crosslinked and hydrated, it can form an electron-conducting redox hydrogel. See Inzelt, G. J. ELECTROANALYTICAL CHEM. AND INTERFACIAL ELECTROCHEMISTRY 1190, 279, 169-78; Horanyi, G., et al. ELECTROCHIMICA ACTA 1988, 33, 947-52; Brahim, S., et al. MICROCHIMICA ACTA 2003, 143, 123-137. In redox hydrogels, electrons diffuse through electron-transferring collisions between hydrated reducible and oxidizable polymer segments. See Heller, A. CURRENT OPINION IN CHEMICAL BIOLOGY 2006, 10, 664-672. A hydrogel is a matrix that does not dissolve in water, but swells in an aqueous solution, increasing its dry weight by at least a factor of 1.5, i.e., adding at least 50% to its weight or volume when hydrated. Preferably it is a matrix that at least doubles its dry weight when hydrated and most preferably it is a matrix that about triples its dry weight. Hydration lowers the local viscosity and reduces attractive coulombic interactions, thereby increasing segmental mobility and electron diffusion. It also increases the permeability of water-soluble ions and molecules.

Glucose-permeable poly(ethylene glycol) diglycidyl ether (PEGDGE)-crosslinked electron-conducting redox hydrogels of $Os^{2+/3+}$ complex-comprising polymers with poly(N-vinylimidazole), and partially N-alkylated poly(4-vinylpyridine) backbones have been studied extensively. See Heller, A. CURRENT OPINION IN CHEMICAL BIOLOGY 2006, 10, 664-672. PEGDGE crosslinks primary, secondary, and tertiary amines, as well as heterocyclic nitrogens. When glucose oxidase (GOx) is co-immobilized in some $Os^{2+/3+}$ complex-comprising hydrogels, it is electrically wired and 3-dimensional glucose electrooxidation catalysts, electrodes at which glucose is electrooxidized at about −0.1 V versus Ag/AgCl and at >1 $mA \cdot cm^{-2}$ are formed. In contrast, when GOx is physically adsorbed on, entrapped in, or electrodeposited on films of metallic or semiconducting PANI, or otherwise integrated on or in PANI films, the glucose electrooxidation current densities are lower. Such is even the case when PANI is covalently bound to a gold substrate through a flavoenzyme thiol, or through nucleophilic thiol attack at o-positions of PANI quinoimine mers. See, e.g. Grant, E., et al. ELECTROANALYSIS 2006, 18, 26-34; Hua, F., et al. MACROMOLECULES 2003, 36, 9971-78; Mano, N., et al. J. ELECTROANALYTICAL CHEMISTRY 2005, 574, 347-57; Mao, F., et al. J. AM. CHEM. SOC 2003, 125, 4951-57; Chaubey, A., et al. ANALYTICA CHIMICA ACTA 2000, 407, 97-103; Borole. D. D., et al. POLYMERS FOR ADVANCED TECHNOLOGIES 2004, 15, 306-12; Garjonyte, R., et al. BIOSENSORS & BIOELECTRONICS 2000, 15, 445-451; Parente, A. H., et al. APPLIED BIOCHEMISTRY AND BIOTECHNOLOGY 1992, 37, 267-73; Cooper, J. C., et al. ELECTROANALYSIS 1993, 5, 385-97; Hall, E. A., et al. ELECTROANALYSIS 1995, 7, 830-37; Pan, X., et al. SENSORS AND ACTUATORS, B: CHEMICAL 2004, B102, 325-30; Han. C.-C., et al. CHEM. MATER. 1999 11, 480-86; Simon, E., et al. J. ELECTROANALYTICAL CHEMISTRY 2002. 538-539, 253-59.

Alternatively, the doping of PANI with polymer acids has been shown, as well, although not in the presence of GOx, and not co-crosslinked with GOx. See, e.g., Yoo, J. E., et al. J. MATER. CHEM. 2007, 17, 1268-75; Lee, K. S., et al. ADV. FUNC. MATER. 2006, 16, 2409.

Historically, high rate electrocatalytic oxidation of glucose required previously-produced polyaniline-containing microrods, and the use of dissolved, rather then immobilized, GOx. Preparation of the microrods was not a single-step process, and required pyrene sulfonic acid-functionalization of single-walled carbon nanotubes, their embedding in aniline and polystyrene sulfonic acid, electropolymerization of the aniline in porous alumina membranes coated with a conductive gold support, and dissolving the alumina membrane. Although the steady state glucose electrooxidation current densities were not reported for such microrods, voltammetric wave heights of 500 µA cm$^{-2}$ at 5 mV s$^{-1}$ scan rate have been observed. See Granot, et al., ELECTROANALYSIS 2006, 18, 26-34.

PANI and its adducts with polymer acids, have been known to form, with glucose oxidase, bioelectrocatalysts catalyzing the electrooxidation of glucose; PANI has also been used with glucose oxidase, the glucose oxidase chemically modified with enzyme-penetrating redox couples or enzyme and conductor-bound, e.g. metal or carbon-nanoparticle bound and chemically modified co-factors, to catalyze the electrooxidation of glucose. Because glucose was not as soluble in these compositions as it is in hydrogels, it was mostly or entirely the conductor-contacting surface at which glucose was electrooxidized.

This invention discloses PANI and enzyme comprising hydrogels in which the enzyme's substrate and the product of the enzyme catalyzed reaction, e.g. glucose and gluconolactone, are both soluble. Their greater solubility provides for faster permeation, i.e. in and out diffusion, wherefore the enzyme molecules co-crosslinked in a thicker 3-dimensional water swollen matrix may participate in the current-generating catalytic oxidation or reduction reactions at, for example, an electrode.

Enzyme comprising bioelectrocatalytic redox hydrogels have been made with polymer backbone-bound metal complexes of iron, osmium, ruthenium and nickel cations. These hydrogels comprised, however, fewer redox centers per unit volume than the PANI and enzyme comprising hydrogels of this invention.

U.S. Pat. No. 5,665,222 discloses a biosensor that is stable at 37° C. The biosensor includes a thermostable peroxidase, for example peroxidase isolated from a soybean, which may be crosslinked with a redox polymer to produce a hydrogen peroxide sensor. The biosensor may also comprise additional immobilized enzymes, such as glucose oxidase.

U.S. Pat. Nos. 6,689,265 and 5,972,199 disclose sensors made using redox hydrogels and a thermostable peroxidase.

U.S. Pat. Nos. 6,881,551; 6,514,718; 6,329,161; 6,162,611; 6,121,009; 6,284,478; and 5,593,852 disclose a small diameter flexible electrodes designed for subcutaneous in vivo amperometric monitoring of glucose that may have "one point" in vivo calibration. The sensors may include glucose oxidase electrically wired to a redox polymer.

U.S. Pat. No. 5,356,786 discloses a sensor that comprises a redox polymer.

U.S. Pat. Nos. 6,576,461 and 6,281,006 relate to affinity assays for the detection of a biological ligand and disclose the use of redox polymers in electrical contact with peroxidase to create a catalyst for the electroreduction of hydrogen peroxide.

U.S. Pat. Nos. 7,018,735; 6,531,239; and 6,294,281 disclose redox hydrogels and enzymes used in fuel cells.

The disclosures of all of the above-cited references are incorporated into the present specification in their entirety.

BRIEF SUMMARY OF THE INVENTION

A crosslinked polymer matrix is created by co-crosslinking (1) an adduct of an polyaniline or substituted polyaniline and a polymer acid; (2) a water-soluble crosslinker; and (3) a redox enzyme. The crosslinked polymer matrix may be hydrated, and may triple its weight upon hydration, and the absorbed water may make it permeable to, for example, glucose.

The polymer acid may exhibit metallic conductivity in the solid state and may comprise sulfonate groups. The electrically conductive polymer and the polymer acid may be present in a molar ratio of from about 1:0.7 to about 1:0.99. The water-soluble crosslinker may be a water-soluble diepoxide, and may be poly(ethylene glycol) diglycidyl ether, present in an amount of from about 2 weight % to about 30 weight %, based upon the dry weight of the crosslinked polymer matrix.

The reaction centers of the redox enzyme may be electrically wired. The redox enzyme may be a flavoenzyme such as glucose oxidase, lactate oxidase, pyruvate oxidase, gluthathione reductase, D-amino acid oxidase, or it can be a heme-enzyme such as horseradish peroxidase, or thermostable soybean peroxidase, or it can be a PQQ-enzyme, like PQQ-glucose dehydrogenase. When the redox enzyme is glucose oxidase, it may be present in an amount of from greater than 0 weight % to less than about 60 weight %, based upon the dry weight of the crosslinked polymer matrix.

The polymer matrix may be capable of catalyzing the oxidation or reduction of a substrate of a redox enzyme at an electrode, for example, where the redox enzyme is glucose or hydrogen peroxide.

When the polymer matrix comprises at least two enzymes, it is preferable that a first enzyme catalyzes a reaction to form the substrate of a second enzyme, and it is further preferable that the second enzyme is a redox enzyme.

The crosslinked polymer matrix of the present invention may be permeable to glucose and may be coated on an electrode such that it may allow for the electrooxidation of glucose at a current density of about 225 µA·cm$^{-2}$ at 40 mM glucose at 0.3 V vs. Ag/AgCl, and may also have an apparent Michaelis-constant obtained from an Edie-Hofstee plot of about 16.8 mM glucose.

The present invention also includes a method for producing the crosslinked polymer matrix of the present invention, which includes (1) an adduct of polyaniline or a ring-substituted polyaniline and a polymer acid; (2) a water-soluble crosslinker; and (3) a redox enzyme, wherein the method includes a step wherein the polyaniline or a ring-substituted polyaniline and the redox enzyme are crosslinked by the water-soluble crosslinker at about a neutral pH. The crosslinked polymer matrix of the present invention may be prepared from a single mixture or from a combination of mixtures of materials which, when combined, comprise a polyaniline or substituted polyaniline, a polymer acid, a water-soluble crosslinker, such as a water-soluble diepoxide, and a redox enzyme. The single mixture or any one of the individual mixtures in the combination of mixtures may individually comprise any or all of the polyaniline or a ring-substituted polyaniline, the polymer acid, the co-crosslinker, and the redox enzyme, so long as the combined mixture from which the crosslinked polymer matrix of the present invention is prepared comprises polyaniline or a ring-substituted polyaniline and a polymer acid, a co-crosslinker, and a redox enzyme. The method may be performed in a single step and/or in a single container. The method may also include a step that includes hydrating the crosslinked polymer matrix of the present invention.

The method may comprise the step of co-crosslinking the electrically-conductive polymer and the redox enzyme by the water-soluble crosslinker at about a neutral pH, and such co-crosslinking may occur after drying the polymer matrix on a corrosion resistant conductor surface.

The present invention includes the crosslinked polymer matrix produced by the method described above. The present invention also includes a redox conductive polymer adduct, swelling after crosslinking to a redox hydrogel.

DETAILED DESCRIPTION OF THE INVENTION

Figure 1:
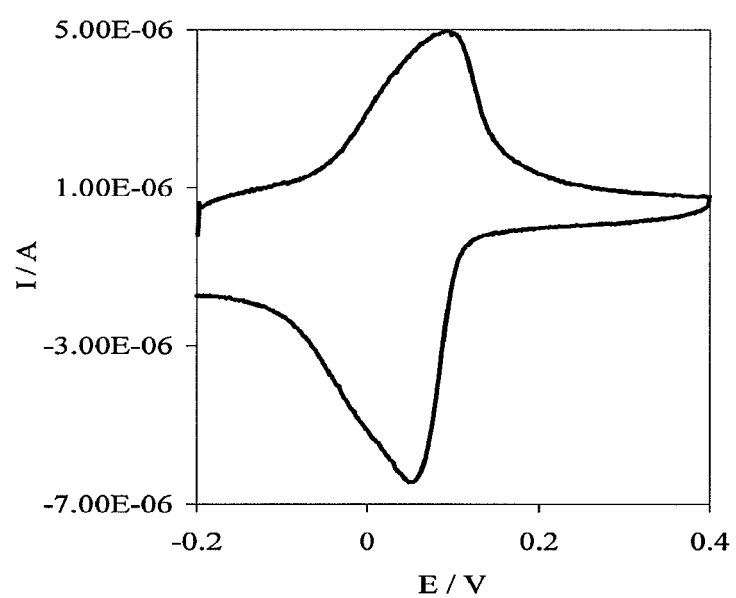
FIG. 1 is the initial cyclic voltammogram of a non-crosslinked PANI-PAAMSA coated vitreous carbon disc electrode at 60 $\mu g \cdot cm^{-2}$ dry-weight loading, at 50 mV/s scan rate, at a pH of 7.2 20 mM phosphate buffer solution wherein the potentials are measured versus that of the Ag/AgCl reference electrode.

The present invention is useful for electrocatalytic oxidation of, for example, glucose, and is useful in an apparatus designed to monitor glucose levels.

Matrix and polymer matrix are synonymous. Both mean a composition formed by crosslinking multiple polymers such that about all polymer molecules are bound to each other. The bonds between the polymer molecules can be electrostatic, as they are in adducts of polyacids/polyanions and polybases/polycations, or they may be covalent.

Diepoxide means a compound having two or more epoxy functions.

Water soluble means a compound dissolving in water at 25° C. to form a solution where its concentration is at least 1 gram per liter, preferably 10 grams per liter.

Water swollen polymer matrix, hydrated polymer matrix, hydrated matrix, hydrated matrix, and redox hydrogel are synonymous. All mean a water-swollen matrix containing an amount of water equaling or exceeding in its weight the dry weight of the matrix.

Redox hydrogel is a hydrated matrix.

Polymer acid can be either the un-dissociated non-ionic, or the dissociated polyanionic polymer, or a polymer comprising both.

Electrically conducting means in the hydrated polymer redox-conductive. In non-hydrated polymers it means a polymer conducting electrons or holes.

Polyaniline (PANI) means polyaniline itself and also any ring-substituted polyaniline, such as poly-meta-toluidine, poly-ortho-toluidine, poly-ortho-fluoroaniline, poly-ortho-methoxyaniline, poly-ortho,ortho'-dimethylaniline.

Flavoenzyme means an enzyme having at least one FAD or FMN co-factor. Glucose oxidase is an example of a flavoenzyme.

Heme-enzyme means an enzyme having at least one heme co-factor. Horseradish peroxidase and soybean peroxidase are examples of heme enzymes.

PQQ-enzyme means an enzyme having at least one pyrroloquinoline quinone cofactor. An example of a PQQ enzyme is PQQ-glucose dehydrogenase.

Neutral pH means a pH of not less than about 5 and not greater than about 8, preferably not less than about 6 and not greater than about 7.5, and most preferably between about 7.2 and about 7.4.

Co-crosslinking means the crosslinking of two or more different macromolecules by the same crosslinker.

Co-crosslinker means a water soluble molecule that crosslinks both the enzyme and the polymer acid adduct of PANI, and therefore crosslinks the enzyme with the polymer acid adduct of PANI.

The crosslinked polymer matrix of the present invention, also termed co-crosslinked polymer or co-crosslinked matrix or crosslinked polymer matrix, may be used as a bioelectrocatalyst on a non-corroding electrode, such as a gold or carbon electrode, and may be in the form of, for example, a film. The gold or carbon may be in the form of a film, preferably a patterned film, deposited on a sheet of an insulator, such as a polymer, exemplified by a polyester.

The crosslinked polymer matrix of the invention comprises (1) an adduct of an electrically-conductive polymer and a polymer acid; (2) a water-soluble crosslinker, capable of crosslinking both proteins and PANI, exemplified by water-soluble diepoxides, and specifically exemplified by poly(ethylene glycol) diglycidyl ether (PEGDGE); and (3) a redox enzyme, wherein the electrically-conductive polymer, the water-soluble crosslinker, and the redox enzyme are co-crosslinked. By the term "co-crosslinked," as used herein, it is meant that the water-soluble crosslinker, such as a diepoxide, crosslinks both the redox enzyme and the PANI-containing polymer adduct.

The bioelectrocatalytic hydrogels formed of the polymer matrices upon their hydration comprise PANI functions, which may conduct electrons and/or electron-vacancies. Typically, when the redox hydrogels are poised at potentials where the glucose electrooxidation current densities are high, their apparent electron diffusion coefficients are greater than about $10^{11}$ cm$^2$ s$^{-1}$. Preferably, they are greater than about $10^{-9}$ cm$^2$ s$^{-1}$ and most preferably they are greater than about $10^{-7}$ cm$^2$ s$^{-1}$.

Fully reduced PANI (leucoemeraldine), the partly or half oxidized PANI (e.g., emeraldine), and the fully oxidized PANI (pernigraniline) states of PANI may be used, as they are generally convertible into each other by electrochemical or chemical oxidation and/or reduction reactions.

Preferably, the molecular weight of the PANI is not less than about 2 kDa and not more than about 500 kDa, before crosslinking, more preferably not less than about 3 kDa and not more than 200 kDa, and most preferably not less than about 5 kDA and not more than 50 kDa.

Suitable substituted PANI's are PANI polymers formed of mers of substituted anilines, in which hydrogen atoms of the aromatic rings are substituted by other atoms or functions. By choosing the substituents, it is possible to adjust the redox potential of the polymer. Electron donating groups, such as methoxy and methyl groups, down-shift the redox potential and make the polymer more reducing. Electron withdrawing groups, such as nitro and nitrile groups, up-shift the redox potential and make the polymer more oxidizing. In general, the preferred ring substituents are not bulky, do not ionize to form anions, but may be protonated to form cations, and are not reactive. Preferred substituents will be obvious to those skilled in the art, and include, for example, small alkyl groups like methyl or ethyl, aryl groups like phenyl, halogens like fluorine, ethers like methoxy, nitrile, and amines like dimethylamino, and nitrogen comprising heterocycles like pyridyl. An example of a substituted PANI-PAAMSA (Poly (2-acrylamido-2-methyl-1-propane sulfonic acid)) that may be used in the present invention is polytoluidine-PAAMSA, which is a ring-methylated aniline polymer. The polytoluidine can be either poly-o-toluidine or poly-m-toluidine. These are, as seen by comparing FIG. 1 with either FIG. 5 or FIG. 6, electrooxidized, and electrooxidized at a more reducing potential than polyaniline-PAAMSA itself, but still sufficiently oxidizing to oxidize flavoenzymes such as glucose oxidase or PQQ-enzymes such as PQQ-glucose dehydrogenase.

A polymer acid suitable for use in the invention is a polymer that, when dissolved in a neutral pH buffered solution, is a polyanion. As the polymer acid, polymers or mixtures of polymers comprising sulfonate groups (sulfonic acid groups) are preferably used. Mixtures of polymer acids may be used in the present invention. For example, styrenesulfonic acid polymer or copolymers comprising styrenesulfonic acid may be used. Poly(2-acrylamido-2-methyl-1-propane sulfonic acid) (PAAMSA) is particularly preferred as the polymer acid. Other exemplary polyanionic polymers include phosphate esters, such as single-stranded RNA or single stranded DNA, and poly(vinyl phosphonate) and its co-polymers.

The polymer acid and the PANI of this invention form electrostatically well bound adducts upon the polymeric acid-templated oxidative polymerization of aniline or a substituted aniline molecule. In such polymerization, multiple monomeric aniline molecules or monomeric functionalized aniline molecules pair by electrostatic bonding with the templating polymer acid, their bonding strengthening as the PANI chains grow and the number of ion pairs with the templating acid increases. Examples include, but are not limited to, PAAMSA-templated PANI or styrenesulfonic acid-templated PANI.

The molecular weight of the polymer acid is preferably not less than about 20 kDa and not more than about 5000 kDa. More preferably, the molecular weight of the polymer acid is from 50 kDa to 2000 kDa, and most preferably, the molecular weight of the polymer acid is from 200 kDa to 1000 kDa.

It is preferred that the adduct of PANI and the polymer acid comprise a small excess of the PANI such that the overall charge of the dissolved polymer is positive at pH 7. The molar ratio of the PANI to the polymer acid is preferably from about 1:0.7 to about 1:0.99, more preferably, from about 1:0.9 to about 1:0.95.

Of course, those of ordinary skill in the art would also recognize additional polymer acids that would be useful in the present invention, along with the conditions under which they would be most useful.

Any water-soluble co-crosslinker of PANI and the enzyme, such as glucose oxidase, can be used. Water soluble diepoxides are examples of such crosslinkers. Poly(ethylene glycol) diglycidyl ether (PEGDGE). is a preferred crosslinker, Mixtures of water-soluble diepoxides can also be used.

Preferably, the PEGDGE has a molecular mass of not less than about 50 Da and not more than about 5000 Da, more preferably between about 100 Da and about 1000 Da, and most preferably of not less than 200 Da and not more than 500 Da.

The water-soluble diepoxide is preferably present in the crosslinked polymer matrix of the present invention in an amount of from about 2 weight % to about 30 weight %, based upon the dry weight of the crosslinked polymer matrix, more preferably, the water-soluble diepoxide is present in an amount of from about 5 weight % to about 20 weight %, most preferably in an amount of from about 6 to about 8 weight %.

Any suitable redox enzyme may be used in the matrices of the present invention, including mixtures of redox enzymes. For example, glucose oxidase (GOx), lactate oxidase, pyruvate oxidase, gluthathione reductase, D-amino acid oxidase, horseradish peroxidase, and thermostable soybean peroxidase may be used.

The substrate of the enzyme may be electrocatalytically oxidized in the reaction electrocatalyzed by the matrix, as is the case, for example, when the substrate is glucose and the enzyme in the matrix is glucose oxidase or PQQ-glucose dehydrogenase; or it may be electrocatalytically reduced, as is the case when the substrate is hydrogen peroxide, when the enzyme is a peroxidase such as soybean peroxidase or horseradish peroxidase. Mixtures of enzymes are useful when one enzyme generates the substrate for another enzyme. For example, acetylcholine esterase catalyzes the generation of choline, which is catalytically electrooxidized when the choline oxidase is one of the matrix enzymes.

Preferably, the GOx is present in an amount less than about 60 weight %, based upon the dry weight of the crosslinked polymer matrix of the present invention, more preferably, in an amount of from about 2 weight % to about 30 weight %, and even more preferably in an amount of from about 5 weight % to about 25 weight %, and most preferably in an amount of from about 15 weight % to about 20 weight %, Suitable hydrophilic conductive filler particles, such as carbon nanofibers, fine carbon fibers, graphite particles, carbon black gold, or nanoparticles may be incorporated in the crosslinked polymer matrix of the present invention in order to reduce their resistivity. Preferably, the added filler particles do not reduce the permeability of the hydrated matrix to the substrate of its enzyme by a factor greater than two.

The crosslinked polymer matrix of the present invention may be prepared by mixing aqueous solutions of the polymer acid-PANI adduct, the enzyme or enzymes, and the water-soluble crosslinker. The mixed aqueous solution may be applied to a non-corroding conductor surface, such as a surface coated with gold, or with a carbon-containing cured polymer. The surface onto which the solution is coated may be made hydrophilic for proper wetting by the coated solution. The non-corroding conductor surface that is coated is usually patterned. The mixed solution of the matrix constituent can be applied by different methods. When a patterned matrix film is desired, the mixed solution can be, for example, screen printed, concentrated, and partially cured until sufficiently viscous for doctor blading then doctor bladed, or it can be sprayed with a shadow-mask applied, or it can be brushed on with a removable mask applied, or it can be applied by stamping. Other application methods include spinning and dipping. After application, the water is allowed to evaporate to concentrate the matrix constituents and accelerate the curing of the matrix by the crosslinking reaction. The temperature of the coated substrate may be raised to a temperature above ambient, but usually below about 50° C., to control and/or accelerate the rate of drying and/or curing. For control, it is usually preferred to dry and cure at a controlled humidity.

The matrix may also be coated on carbon fibers woven to form a cloth, or onto non-woven carbon cloth if the fibers are glued to each other. The preferred cloths are macroporous, their void fraction exceeding 30%, preferably 50%, and most preferably 60%. Furthermore, the fiber surfaces may be made preferably hydrophilic prior to the application of the matrix-forming mixture.

Glucose oxidase may be co-crosslinked with the electrically-conductive polymer and the water-soluble diepoxide by, for example, a procedure similar to the process disclosed within *Long Tethers Binding Redox Centers to Polymer Backbones Enhance Electron Transport in Enzyme "Wiring" Hydrogels*, by Fei Mao, Nicolas Mano, and Adam Heller, J. Amer. Chem. Soc. 2003, 125, 4951-4957, the disclosure of which is incorporated by reference into the present specification in its entirety. That article discloses the binding of a wired GOx electrocatalyst in an $Os^{2+/3+}$ complex-comprising redox polymer.

If multiple separate constituent solutions are used to prepare the crosslinked polymer matrix of the invention, it is preferred that one solution contains the adduct of the PANI and the polymer acid; a second contains the enzyme or enzymes; and a third contains the water-soluble crosslinker. The preferred order of mixing the solutions is mixing the first with the second, then adding the third.

The co-crosslinking of the crosslinked polymer matrix of the present invention is preferably performed at a neutral pH.

A further aspect of the invention is an electrochemical blood glucose test strip, incorporating a crosslinked PANI-PAAMSA-enzyme matrix, and used to assay glucose by coulometric analysis. In this embodiment, the crosslinked PANI-PAAMSA-enzyme matrix is coated onto the working electrode of a blood glucose test strip, for example, the FreeStyle™ blood glucose test strip of Abbott Diabetes Care. When a blood sample enters the strip, a sufficient operating potential is applied to the strip to effect the oxidation of all or most of the glucose in said blood sample, and the glucose concentration is determined by integration of the resulting charge.

The following Example illustrates the invention, but should not be interpreted to limit the invention.

EXAMPLE

Figure 4:
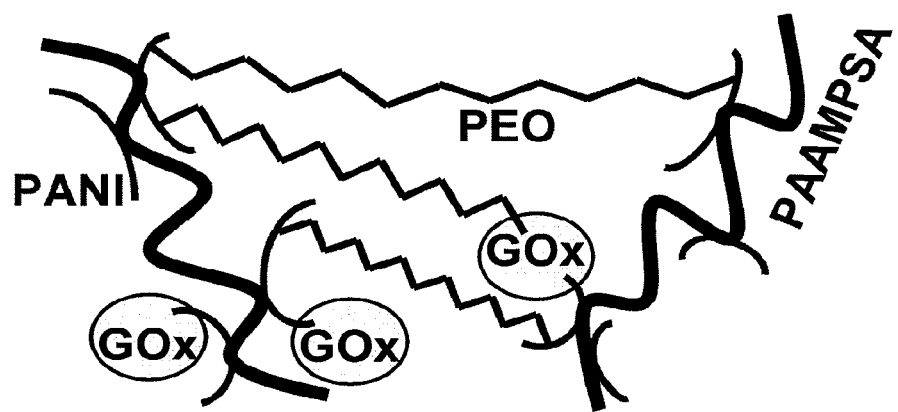
FIG. 4 is a graphical representation of the co-crosslinked polymer matrix of the present invention.

A polyaniline-based, electron-conducting, glucose permeable redox hydrogel was formed in one step at pH 7.2 by crosslinking a PAAMSA templated PANI with PEGDGE. Incorporation of glucose oxidase in the hydrogel by co-crosslinking in the same step led to electrical wiring of the enzyme and led to the formation of a glucose electrooxidation catalyst, allowing the electrooxidation of glucose at a current density of 225 $\mu A \cdot cm^{-2}$ at 0.3 V versus Ag/AgCl. FIG. 4 is a representation of the redox hydrogel.

A PANI-GOx bioelectrocatalyst was prepared, according to the following description, at a neutral pH in one pot in a single step. Emeraldine PANI was used as the electrically conducting polymer, PAAMSA was used as the polymer acid, PEGDGE was used as the water-soluble diepoxide, and GOx was used as the redox enzyme.

Figure 5:
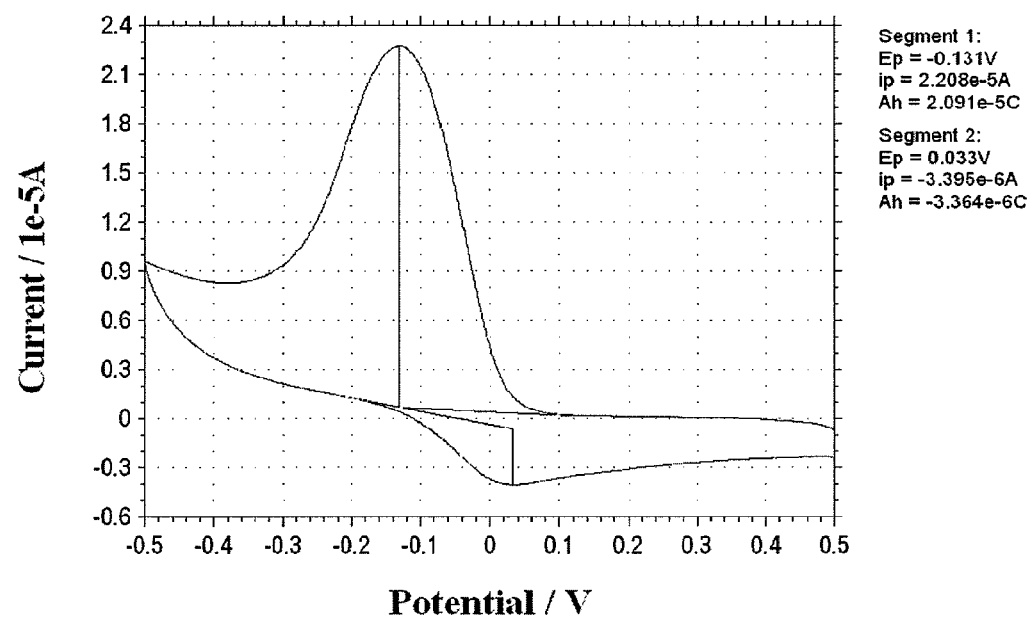
FIG. 5 is a first scan cyclic voltammogram of a non-crosslinked poly-o-toluidine-PAAMSA film on a vitreous carbon electrode at 100 mV/s scan rate in a pH 7, 20 mM phosphate buffer solution, potentials being measured versus the Ag/AgCl reference electrode.
Figure 6:
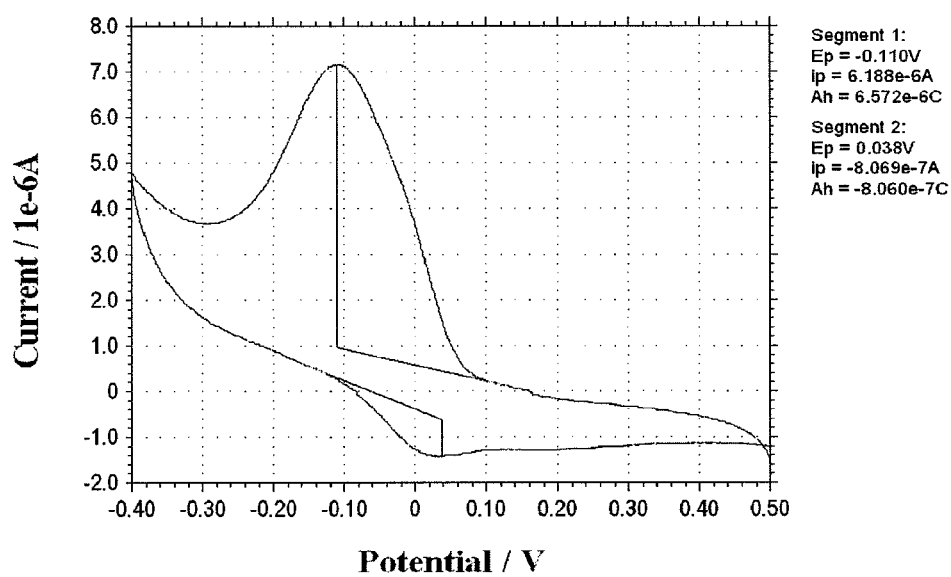
FIG. 6 is a first scan cyclic voltammogram of a non-crosslinked poly-m-toluidine-PAAMSA film on a vitreous carbon electrode at 100 mV/s scan rate in a pH 7, 20 mM phosphate buffer solution, potentials being measured versus the Ag/AgCl reference electrode.

The emeraldine PANI used was made by oxidative template polymerization of aniline on water-dissolved poly(2-acrylamido-2-methyl-1-propane sulfonic acid), PAAMSA with ammonium persulfate. The conductivity of the PANI-PAAMSA salt was 0.430±0.019 S/cm after the purified aqueous polymer salt dispersion was spin- or drop-cast and dehydrated. The molecular mass of the PAAMSA was 724 kDa and solid-state NMR showed that the PANI segments were 8-20 repeat units long. Elemental analysis and x-ray photoelectron spectroscopy of the purified PANI-PAAMSA indicated an aniline:sulfonic acid molar ratio of about 1:0.9. To show that un-crosslinked PANI/PAAMSA is a typical diffusionally mobile redox couple, glassy carbon electrodes were coated with 10 μL of a 5 weight % aqueous solution of the polymer (60 $\mu g \cdot cm^{-2}$ initial dry-weight based loading) and allowed to dry. FIG. 1 shows the initial cyclic voltammograms of the PANI/PAAMSA-modified electrode under argon in a pH 7.2 phosphate buffer solution (PBS) at 37.5° C. The voltammogram is characteristic of the doped PANI emeraldine redox couple, peaking at +0.1 V vs. Ag/AgCl. Though the film slowly dissolved in the absence of a crosslinker, the voltammetric wave was stable at pH 7.2 and the anodic peak current increased linearly with scan rates up to 400 $mV \cdot s^{-1}$, as expected for a weakly surface bound redox couple. For the sake of comparison, FIGS. 5 and 6 show cyclic voltammograms for poly-o-toluidine-PAAMSA films and poly-m-toluidine-PAAMSA films, respectively.

Figure 2:
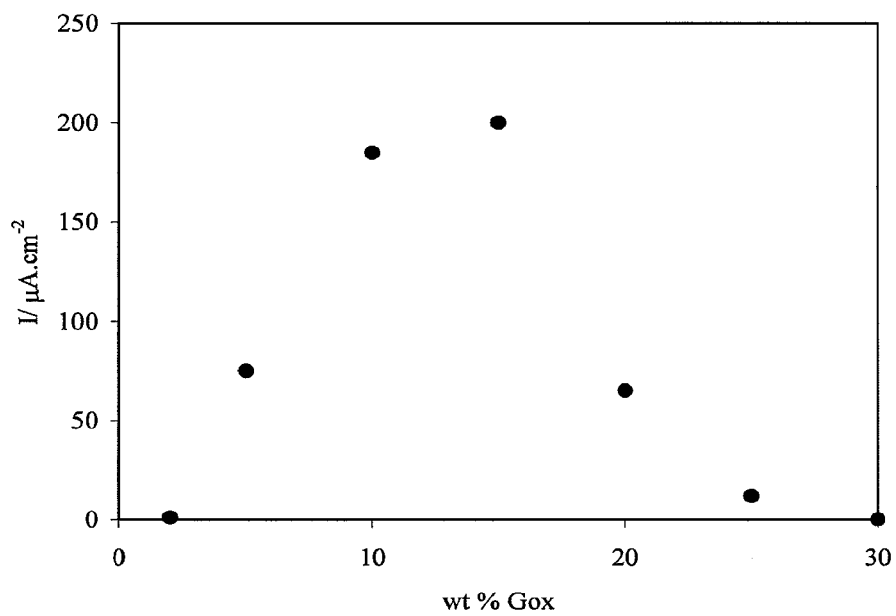
FIG. 2 is a chart illustrating the dependence of the current density on the glucose oxidase weight percentage in the about dry PEGDGE-crosslinked PANI-PAAMSA-glucose oxidase matrix when the glucose concentration is maintained at 32 mM.

To show that a hydrogel is formed upon crosslinking the PANI-PAAMSA with a 400 Da PEGDGE, through reaction with PANI nitrogens, the water uptake at 0.1 $g \cdot cm^{-2}$ dry-weight loading of the films in multiple hydration-dehydration cycles was measured. To form the films, aqueous polymer solutions were mixed at 1:0.07 w/w PANI-PAAMSA/PEGDGE ratio, deposited on microscope slides, and cured in ambient air for 48 hours. The increase/decrease in mass in cycles of (a) immersion in de-ionized water for 1 minute; (b) tilting to drain the water; (c) contacting the surface with absorbent paper tissue (KIMWIPE®) to remove surface water not bound in the hydrogel; (d) air-drying; and (e) repeat rehydration was measured. In three sets of measurements on different samples, the mass of the water added on swelling and lost upon drying was 2±0.2 times the weight of the dry PANI-PAAMSA/PEGDGE. To show that the hydrogel is permeable to glucose and is electrically wired to GOx, films were made by mixing droplets of known volume and concentration of aqueous solutions of PANI-PAAMSA (in pH 7.4, 0.1 M phosphate buffer), GOx (in pH 7.2, 0.1 M phosphate buffer) and PEGDGE (in de-ionized water) on vitreous carbon electrodes. The films were made as earlier described for an $Os^{2+/3+}$ complex-comprising redox polymer-wired GOx electrocatalyst, except that the $Os^{2+/3+}$ complex-based polymer was replaced by PANI-PAAMSA, the solution of which was now diluted tenfold with pH 7.4 0.1 M phosphate buffer. See the above-mentioned article by Fei Mao, Nicolas Mano, and Adam Heller, entitled *Long Tethers Binding Redox Centers to Polymer Backbones Enhance Electron Transport in Enzyme "Wiring" Hydrogels*. The films were cured for >18 hours at ambient temperature. FIG. 2 shows the dependence of the glucose electrooxidation current density on the GOx weight percentage in the dry films in pH 7.2, 32 mM glucose, 20 mM phosphate buffer at 37° C. at a fixed loading of 0.8 $mg \cdot cm^{-2}$ ($\rho$=1.39 $g \cdot cm^{-3}$). In the 2-15 weight % GOx range, the current density increased with the weight percentage of GOx, reaching 200 $\mu A \cdot cm^2$ at 15 weight %. At higher GOx content the current density declined. The decline is attributed to de-swelling when the polyanionic GOx neutralizes the residual net positive charge of PANI-PAAMSA.

Figure 3:
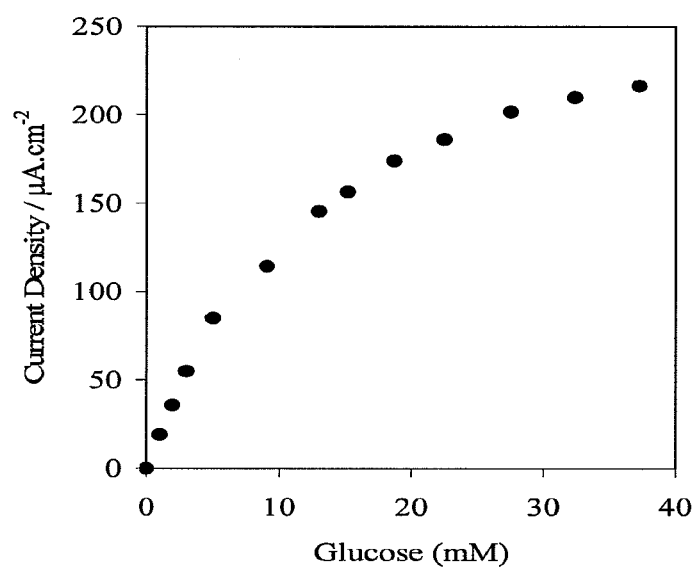
FIG. 3 is a chart illustrating the dependence of the steady-state current density on glucose concentration for a PEGDGE-co-crosslinked PANI-PAAMSA-glucose oxidase matrix-coated vitreous carbon disk electrode poised at about +0.3 V versus Ag/AgCl, rotating at about 500 rpm under argon.

FIG. 3 shows the dependence of the current density on glucose concentration under argon for an electrode that was poised at 0.3 V versus Ag/AgCl in a PBS buffer. The current density was about 225 $\mu A \cdot cm^{-2}$ at 40 mM glucose. The apparent Michaelis-constant, $K'_M$, obtained from an Edie-Hofstee plot was about 16.8 mM glucose.

What is claimed is:

1. A method for producing a crosslinked polymeric matrix, the method comprising co-crosslinking a polyaniline, a polymer acid and a redox enzyme with a crosslinker to produce the crosslinked polymeric matrix.

2. The method according to claim 1, wherein the polyaniline is a ring-substituted polyaniline.

3. The method according to claim 2, wherein the ring-substituted polyaniline is a compound selected from the group consisting of poly-meta-toluidine, poly-ortho-toluidine, poly-ortho-fluoroaniline, poly-ortho-methoxyaniline, poly-ortho,ortho'-dimethylaniline.

4. The method according to claim 1, wherein the polymer acid is poly(2-acrylamido-2-methyl-propane sulfonic acid) (PAAMSA).

5. The method according to claim 4, wherein the polyaniline and PAAMSA are present in a molar ratio of from about 1:0.7 to about 1:0.99.

6. The method according to claim 1, wherein the crosslinker is a water soluble crosslinker.

7. The method according to claim 6, wherein the water soluble crosslinker comprises poly(ethylene glycol) diglycidyl ether.

8. The method according to claim 7, wherein the method comprises crosslinking the polymeric matrix at neutral pH.

9. The method according to claim 8, wherein the method comprises crosslinking the polymeric matrix on a corrosion resistant conductor surface.

10. The method according to claim 6, wherein the water-soluble crosslinker is present in an amount of from about 2 weight % to about 30 weight %, based upon the dry weight of the polymer matrix.

11. The method according to claim 1, wherein the crosslinked polymeric matrix is a hydrogel.

12. The method according to claim 11, wherein the method further comprises hydrating the hydrogel.

13. The method according to claim 1, wherein the redox enzyme is selected from the group consisting of a flavoenzyme, a heme enzyme, and a pyrroloquinoline quinone (PQQ) enzyme.

14. The method according to claim 1, wherein the redox enzyme is selected from the group consisting of glucose oxidase, glucose dehydrogenase, and peroxidase.

15. The electrochemical sensor according to claim 1, wherein the redox enzyme of the crosslinked polymer matrix has an apparent Michaelis-constant obtained from an Edi-Hofstee plot of greater than 10 mM glucose.

16. The method according to claim 1, wherein the crosslinked polymer matrix comprises at least two enzymes, wherein a first enzyme is an enzyme which catalyzes a reaction to form a substrate for a second enzyme, and wherein the second enzyme is a redox enzyme.

17. The method according to claim 1, wherein the redox enzyme is present in an amount of from greater than 0 weight % to about 60 weight %, based upon the dry weight of the polymer matrix.

* * * * *

UNITED STATES PATENT AND TRADEMARK OFFICE
CERTIFICATE OF CORRECTION

PATENT NO. : 8,703,458 B2  
APPLICATION NO. : 13/756009  
DATED : April 22, 2014  
INVENTOR(S) : Adam Heller et al.

Page 1 of 1

It is certified that error appears in the above-identified patent and that said Letters Patent is hereby corrected as shown below:

Please replace the existing Statement Regarding Federally Sponsored Research, Col. 1, lines 5-8 of the specification, with the following:

--STATEMENT REGARDING FEDERALLY SPONSORED RESEARCH
This invention was made with government support under Grant no. N00014-02-1-0144 awarded by the Office of Naval Research. The government has certain rights in the invention.--

Signed and Sealed this
Twenty-sixth Day of May, 2015

Michelle K. Lee
*Director of the United States Patent and Trademark Office*